ns Patent Number: 4,655,973
Date of Patent: Apr. 7, 1987

CONJUGATED POLYPRENYLCARBOXYLIC ACIDS AND THEIR DERIVATIVES

[75] Inventors: Isao Yamatsu, Kawaguchi; Yuichi Inai, Tokyo; Shinya Abe, Nakamura; Takeshi Suzuki, Abiko; Yoshikazu Suzuki, Ichinomiya; Osamu Tagaya, Gifu; Kouichi Suzuki, Kakamigahara; Kouichi Abe, Fuchu; Kouji Yamada, Tokyo, all of Japan

[73] Assignee: Eisai Co., Ltd., Tokyo, Japan

[21] Appl. No.: 260,869

[22] Filed: May 6, 1981

[30] Foreign Application Priority Data

Dec. 24, 1980 [JP] Japan ................. 55-182115

[51] Int. Cl.$^4$ ................. C07C 103/133; C07C 103/58
[52] U.S. Cl. ................. 260/404; 260/404.5; 260/410.9 R; 260/413
[58] Field of Search ............. 260/404, 405.5, 410.9 R, 260/413 L

[56] References Cited

U.S. PATENT DOCUMENTS

| | | | |
|---|---|---|---|
| 3,712,922 | 1/1973 | Henrick et al. | 260/413 L X |
| 4,107,193 | 8/1978 | Kijima et al. | 260/413 L X |
| 4,116,955 | 9/1978 | Ichikawa et al. | 260/404 X |
| 4,199,519 | 4/1980 | Mishima et al. | 260/413 L |
| 4,260,551 | 4/1981 | Mishima et al. | 560/224 X |
| 4,293,500 | 10/1981 | Morel | 260/410.9 R |

Primary Examiner—Charles F. Warren
Attorney, Agent, or Firm—Flynn, Thiel, Boutell & Tanis

[57] ABSTRACT

A conjugated polyprenylcarboxylic acid and its derivative having the formula:

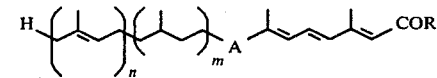

in which each of n and m is 0, 1 or 2, n+m is 1 or 2, A is

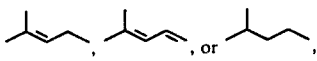

and R is the hydroxyl group, a lower alkoxy group or

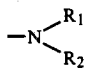

wherein each of $R_1$ and $R_2$ represents the hydrogen atom, a lower alkyl group, or an aryl group; provided that R is

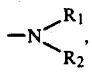

if A is

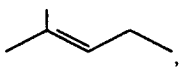

n is 1 and m is 0.

6 Claims, No Drawings

CONJUGATED POLYPRENYLCARBOXYLIC ACIDS AND THEIR DERIVATIVES

This invention relates to a novel conjugated polyprenylcarboxylic acid and its derivative having the formula (I):

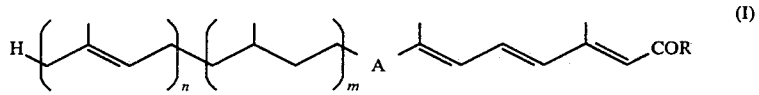

in which each of n and m is 0, 1 or 2, n+m is 1 or 2, A is

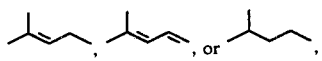

and R is the hydroxyl group, a lower alkoxy group or

wherein each of $R_1$ and $R_2$ represents the hydrogen atom, a lower alkyl group, or an aryl group; provided R is

if A is

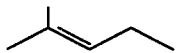

n is 1 and m is 0.

Examples of the lower alkoxy groups represented by R in the above-mentioned formula (I) include methoxy, ethoxy, i-propoxy, n-propoxy, t-butoxy and n-butoxy. Examples of the lower alkyl groups represented by $R_1$ and $R_2$ includes methyl, ethyl, i-propyl, n-propyl, t-butyl and n-butyl, and examples of the aryl groups represented by $R_1$ and $R_2$ include phenyl and a phenyl group having substituent groups such as hydroxyl, a lower alkyl group or halogen. If R in the formula (I) is hydroxyl, the compound may be in the form of a salt such as sodium or potassium salt.

W. Bollag, et al. reported in Europ. J. Cancer, Vol. 10, p. 731 (1974) that retinoides such as ethyl 9-(2,3,6-trimethyl-4-methoxyphenyl)-3,7-dimethyl-2,5,6,8-nonatetraenoate have anti-cancer activity. These retinoide compounds, however, are highly toxic, and further have problems such as causing hypervitaminosis of Vitamin A when administered.

The polyprenylcarboxylic acids and their derivatives of the formula (I) show remarkable anti-cancer activity and are highly safe compounds. For instance, these polyprenylcarboxylic acids and their derivatives do not cause hypervitaminosis of Vitamin A. Further toxicities of the polyprenylcarboxylic acids and their derivatives of the formula (I) other than the hypervitaminosis are also at low level.

Moreover, the polyprenylcarboxylic acids and their derivatives of the formula (I) are of value as therapeutic agents for treatment of skin diseases with keratinization or treatment of allergic or inflammatory skin diseases, such as psoriasis, acne, acne vulgaris, Darier's disease, palmoplantar pustulosis, lichen plasnus, ichthyosis, erythroderma, pityriasis rubra pilasis, and keratosis sensilis, as well as the therapeutic agents for prevention and treatment of cancer and precancerous conditions.

The conjugated polyprenylcarboxylic acid and its derivative of the formula (I) can be prepared by the following processes.

PROCESS A (1) A compound having the formula (II):

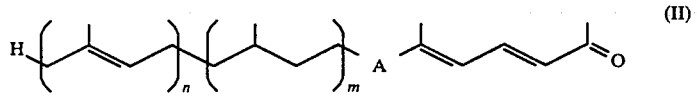

in which n, m and A have the same meanings as defined hereinbefore, and a Wittig reagent derived from a compound having the formula (III):

in which X represents a halogen atom, and $R_3$ represents a lower alkyl group, are reacted to give the polyprenylcarboxylic acid derivative having the formula (I)-1:

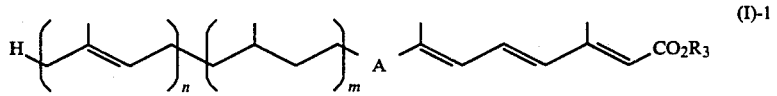

in which n, m, A and $R_3$ have the same meanings as defined above.

(2) The polyprenylcarboxylic acid derivative of the formula (I)-1, if desired, can be hydrolyzed to give the polyprenylcarboxylic acid having the formula (I)-2:

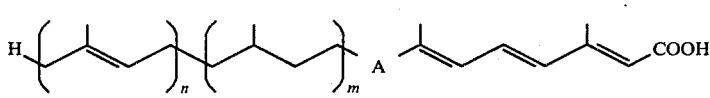 (I)-2 in which n, m and A have the same meanings as defined above.

Examples of the Wittig reagents employed in the above-described (1) stage and derived from a compound of the formula (III) include phosphoric compounds produced by the reaction between the compound of the formula (III) and triphenylphosphine, phenyldialkoxyphosphine, trialkylphosphite, or the like. The preparation of the reagent and the wittig reaction employing the reagent can be carried out by the conventional methods such as the method given by Wadworth, et al. in J. Am. Chem. Soc., Vol. 83, p. 1733 (1961), the method given by Greenwald, et al. in J. Org. Chem., Vol. 28, p. 1128 (1963), and the method given by Horner, et al. in Ber., Vol. 95, p. 581 (1962).

In the above-described (2) stage, the hydrolysis can be carried out in the presence of a base generally employed for hydrolysis of carboxylic acid esters, such as sodium hydroxide and potassium hydroxide.

PROCESS B (1) A compound having the formula (V):

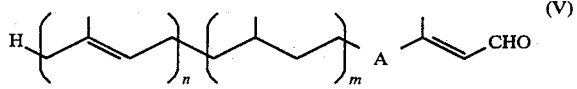 (V)

in which n, m and A have the same meanings as defined hereinbefore, and a Wittig reagent derived from a compound having the formula (VI):

 (VI)

in which X and R₃ have the same meanings as defined above, are reacted to give the polyprenylcarboxylic acid derivative having the above-mentioned formula (I)-1.

(2) The polyprenylcarboxylic acid derivative of the formula (I)-1, if desired, can be hydrolyzed to give the polyprenylcarboxylic acid having the above-mentioned formula (I)-2.

Each of the procedures in the above-described stages (1) and (2) can be carried out in the same manner as in Process A.

PROCESS C (1) A compound having the formula (VII):

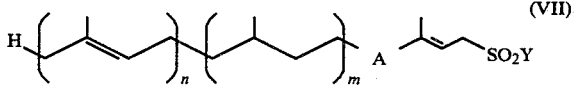 (VII)

in which n, m and A have the same meanings as defined hereinbefore, and Y represents a lower alkyl group or an aryl group, and the compound of the above-mentioned formula (VI) are reacted to give a compound having the formula (VIII):

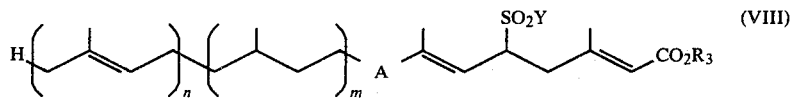 (VIII)

in which n, m, A, Y and R₃ have the same meanings as defined above; and then (2) the compound of the formula (VIII) is subjected to a reaction for removal of the sulfinic acid group and hydrolysis in the presence of a base to give the compound of the aforementioned formula (I)-2.

The above-mentioned stage (1) is carried out in the presence of a base. Examples of the bases include n-butyllithium and phenyllithium. Examples of the reaction solvents include tetrahydrofuran, diethyl ether and 1,2-dimethoxyethane. The reaction is generally carried out at a temperature lower than room temperature.

The above-mentioned stage (2) can be carried out in the same manner as the stage (2) of the aforementioned Process A.

If the polyprenylcarboxylic acid derivative in the amide form is desired, the polyprenylcarboxylic acid of the formula (I)-2 obtained in one of the Processes A, B and C is reacted with a compound having the formula (IX):

 (IX)

in which R₁ and R₂ have the same meanings as defined hereinbefore, to give the desired amide derivative that is, also, included in the polyprenylcarboxylic acid derivative of the invention. The above-described reaction is preferably carried out in the presence of a condensation reagent such as ethyl chlorocarbonate.

Examples of the polyprenylcarboxylic acids and their derivatives of the formula (I) according to the invention include:
3,7,11,15,19-pentamethyl-2,4,6,10,14,18-eicosahexaenoic aicd
3,7,11,15-tetramethyl-2,4,6,14-hexadecatetraenoic acid
3,7,11,15-tetramethyl-2,4,6-hexadecatrienoic acid
3,7,11,15-tetramethyl-2,4,6,8,10,14-hexadecahexaenoic acid
3,7,11,15-tetramethyl-2,4,6,10-hexadecatetraenoic acid
3,7,11,15,19-pentamethyl-2,4,6,8,10,14,18-eicosaheptaenoic acid
3,7,11,15,19-pentamethyl-2,4,6,10,18-eicosapentaenoic acid
ethyl 3,7,11,15-tetramethyl-2,4,6-hexadecatrienoate
ethyl-3,7,11,15,19-pentamethyl-2,4,6,10,14,18-eicosahexaenoate
methyl 3,7,11,15,19-pentamethyl-2,4,6,10,14,18-eicosahexaenoate ethyl 3,7,11,15-tetramethyl-2,4,6,8,10,14-hexadecahexaenoate
3,7,11,15-tetramethyl-2,4,6,10,14-hexadecapentaenoamide
N-(p-hyroxyphenyl)-3,7,11,15-tetramethyl-2,4,6,10,14-hexadecapentaenoamide
N-ethyl-3,7,11,15-tetramethyl-2,4,6,10,14-hexadecapentaenoamide
N,N-dimethyl-3,7,11,15-tetramethyl-2,4,6,10,14-hexadecapentaenoamide
N-ethyl-3,7,11,15-tetramethyl-2,4,6,8,10,14-hexadecahexaenoamide
N-ethyl-3,7,11,15,19-pentamethyl-2,4,6,10,14,18-eicosahexaenoamide The results of the pharmacological tests and toxicity tests on the polyprenyl compounds of the formula (I) are set forth below.

PHARMACOLOGICAL TESTS (ANTI-CANCER ACTIVITY)

(1) Test procedure

A mouse (ICR strain, female, 60 days age) was shaved at the back of neck (to the extent to 5 cm²). 7,12-Dimethylbenzo[2]-anthracene was dissolved in acetone to give 75 mg./100 ml. solution. The so prepared solution was applied to the mouse on the 60th aged day and further on the 75th aged day in the amount of 0.2 ml. per mouse.

Crotonic oil was dissolved in acetone to give 250 mg./100 ml. solution, and the so prepared solution was applied to the mouse in the amount of 0.02 ml. per mouse, twice a week until the treatment was started. When 3-7 papillomata (diameter of 3-8 mm. for each, and total diameter of 30-60 mm.) were produced for a mouse, the treatment was started.

The compound to be tested (test compound) was dissolved in groundnut oil to give 20 mg./ml. solution, and administered orally to the mouse. The solution was administered 10 times for 14 days (once a day), and the diameters of the papillomata were measured on the 14th day to determine the total diameter for each mouse. Ratio of increase or decrease of the papillomata was calculated from the total diameter on the 14th day and the total diameter measured prior to the starting of administration of the test compound. This value was adopted for evaluating the anti-cancer activity.

(2) Results

TABLE 1

| Test Compound | Number of mouse | Ratio of increase or decrease of papillomata (%) |
|---|---|---|
| Groundnut only (Control) | 3 | +17.1 |
| 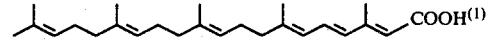 COOH⁽¹⁾ | 5 | −24.0 |
| 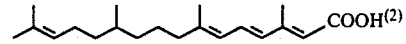 COOH⁽²⁾ | 4 | −19.5 |
| 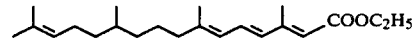 COOC₂H₅⁽³⁾ | 4 | −10.2 |
| 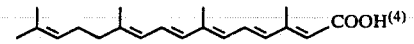 COOH⁽⁴⁾ | 5 | −26.3 |
| 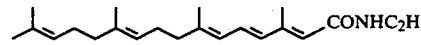 CONHC₂H₅⁽⁵⁾ | 5 | −25.5 |

Remarks:
The compounds identified by the structural formulae in Table 1 correspond to the following polyprenyl compounds.
⁽¹⁾3,7,11,15,19-pentamethyl-2,4,6,10,14,18-eicosahexaenoic acid
⁽²⁾3,7,11,15-tetramethyl-2,4,6,14-hexadecatetraenoic acid
⁽³⁾ethyl 3,7,11,15-tetramethyl-2,4,6,14-hexadecatetraenoate
⁽⁴⁾3,7,11,15-tetramethyl-2,4,6,8,10,14-hexadecahexaenoic acid
⁽⁵⁾3,7,11,15-tetramethyl-2,4,6,10,14-hexadecapentaenoamide As seen from the data in Table 1, the polyprenyl compounds of the formula (I) are effective against the papilloma.

TOXICITY TESTS

(1) Test procedure

The test compound was administered repeatedly to a group of 6 mice (ICR strain, female) for 14 days in the dosage of 200 mg./kg./day. In the course of the administration procedures, increase or decrease of the weight of the mouse, occurance of death, etc. were observed.

(2) Test compound

The compounds set forth in the above Table 1 were employed.

(3) Test results

No death was observed. Decrease of the weight was not observed, and a little increase of the weight was observed. No symptoms indicating the effects of side sections, such as falling-out of hair, cyanosis, etc., were observed.

The decrease of the weight and the falling-out of hair are known as indicating the hypervitaminosis of Vitamin A. Accordingly, the results are considered to indicate that the polyprenyl compounds of the formula (I) do not cause the hypervitaminosis of Vitamin A.

In view of the pharmacological test results and the toxicity test results as described hereinbefore, the polyprenyl compounds of the formula (I) are judged to be of high safety and to be of value as anti-cancer agents for prevention and treatment of cancer and precancerous conditions.

For the application as the anti-cancer agent, the polyprenyl compound of the formula (I) can be administered orally in the form of powder, granule, pellet, hard capsule, etc., or parenterally in the form of ointment, suppository, injection solution, etc. The dosage is generally set in the range of 40 mg. to 4 g./day for adult. If the polyprenyl compound of the formula (I) is applied to the form of an external preparation, the dosage can be varied depending on the largeness of area on the affected part. The above-mentioned preparations can be prepared from the polyprenyl compound and generally employable carriers for the medical used by utilizing the conventional methods.

The following examples will illustrate processes for the preparations of the polyprenylcarboxylic acids and their derivatives of the formula (I) according to the invention, but these examples are not given to restrict the invention.

EXAMPLE 1

Ethyl 3,7,11,15-tetramethyl-2,4,6,14-hexadecatetraenoate

To a suspension of 2.5 g. of 55% sodium hydride (in oil) in 30 ml. of n-hexane was added 13.6 g. of triethyl phosphonoacetate. The mixture was then heated under reflux, and 10 g. of 6,10,14-trimethyl-3,5,13-pentadecatrien-2-one was added dropwise to the mixture under stirring. After 30 minutes, the reaction liquid was poured into 100 ml. of ice-water, and then 200 ml. of n-hexane was added for extraction. The n-hexane phase was separated, washed with two 50 ml. portions of a mixture of methanol and water (2:1), and concentrated. The so obtained concentrate was purified by the silica gel column chromatography to give 9.0 g. of the desired product as an oil.

| Analysis for $C_{22}H_{36}O_2$ | | |
|---|---|---|
| | C | H |
| Calculated (%) | 79.46 | 10.92 |
| Found (%) | 79.74 | 11.04 |

NMR spectrum ($\delta$, CDCl$_3$): 0.87 (3H, d, J=6 Hz), 1.28 (3H, t, J=7 Hz), 1.0–1.6 (7H), 1.61. (3H, s), 1.69 (3H, s), 1.85 (3H, s), 1.9–2.4 (4H), 23.4 (3H, d, J=1 Hz), 4.17 (2H, q, J=7 Hz), 5.10 (1H, t, J=7 Hz), 5.75 (1H, bs), 5.95 (1H, d, J=11 Hz), 6.16 (1H, d, J=15 Hz), 6.86 (1H, dd, J=15 Hz, 11 Hz).
Mass spectrum (m/e): 332 (M+).

EXAMPLE 2

3,7,11,15-Tetramethyl-2,4,6,14-hexadecatetraenoic acid 8.0 g. of the ethyl 3,7,11,15-tetramethyl-2,4,6,14-hexadecatetraenoate obtained in the previous. Example 1 was added to a solution of 3.2 g. of potassium hydroxide in 20 ml. of isopropyl alcohol, and the mixture was stirred at 50° C. for 1 hour. The reaction liquid was then poured into ice-water, made acidic by addition of hydrochloric acid, and extracted with 50 ml. of diethyl ether. The ether phase was washed with water, dried over magnesium sulfate, and concentrated to give 7. g. of an oil. The oil was dissolved in 40 ml. of n-hexane and crystallized at −20° C. to give 3.1 g. of the desired product as white crystals.
M.p.: 60°–62° C.

| Analysis for $C_{20}H_{32}O_2$ | | |
|---|---|---|
| | C | H |
| Calculated (%) | 78.89 | 10.59 |
| Found (%) | 78.77 | 10.63 |

NMR spectrum ($\delta$, CDCl$_3$): 0.87 (3H, d, J=6 Hz), 1.0–1.6 (7H), 1.60 (3H, s), 1.69 (3H, s), 1.85 (3H, s) 1.9–2.3 (4H), 2.34 (3H, d, J=1 Hz), 5.10 (1H, t, J=7 Hz), 5.77 (1H, bs), 5.97 (1H, d, J=11 Hz), 6.20 (1H, d, J=15 Hz), 6.91 (1H, dd, J=15 Hz, 11 Hz), 9.6 (1H, b).
Mass spectrum (m/e): 304 (M+).

EXAMPLE 3

3,7,11,15-Tetramethyl-2,4,6,8,10,14-hexadecahexaenoic acid

To a suspension of 30.0 g of sodium ethoxide in 300 ml. of tetrahydrofuran was added 118 g. of diethyl 3-ethoxycarbonyl-2-methyl-2-propenylphosphonate. To the mixture was added 67 g. of 3,7,11-trimethyl-2,4,6,10-dodecatetraen-1-al under stirring, chilling with ice and shielding from the light. After 1 hour, the reaction liquid was poured into 1 liter of water, and 1 liter of n-hexane was added for extraction. The n-hexane phase was separated, washed with two 100 ml. portions of a mixture of methanol and water (2:1), and concentrated to give 99 g. of a concentrate. To a refluxing solution of 8.2 g. of potassium hydroxide and 80 ml. of ispropyl alcohol was added 21 g. of the concentrate under shielding from the light. After 15 minutes, the reaction liquid was poured into 300 ml. of ice-water, made acidic by addition of hydrochloric acid, and extracted with 300 ml. of diethyl ether. The extract was washed with three 100 ml. portions of water, dried over magnesium sulfate, and evaporated to remove the solvent. The residue was dissolved in 200 ml. of n-hexane and chilled to −20° C. to crystallize. There was obtained 9.8 g. of the desired product as pale yellow crystals.

| Analysis for $C_{20}H_{28}O_2$ | | |
|---|---|---|
| | C | H |
| Calculated (%) | 79.95 | 9.39 |
| Found (%) | 80.22 | 9.47 |

NMR spectrum ($\delta$, CDCl$_3$): 1.63 (3H, s), 1.69 (3H, s), 1.84 (3H, s), 1.99 (3H, s), 2.0–2.3 (4H), 2.36 (3H, s), 5.15 (1H, m), 5.6–7.2 (7H, m), 1.04 (1H, b).
Mass spectrum (m/e): 300 (M+).

EXAMPLE 4

3,7,11,15,19-Pentamethyl-2,4,6,10,14,18-eicosahexaenoic acid

In 100 ml. of tetrahydrofuran was dissolved 12 g. of 1-p-tolylsulfonyl-3,7,11,15-tetramethyl-2,6,10,14-hexadecatetraene, and the solution was chilled to −50° C. To the solution was added dropwise 18.5 ml. of 15% n-butyllithium-n-hexane solution under stirring and in a stream of nitrogen, maintaining the temperature of the solution at −50° C. Then, 300 ml. of tetrahydrofuran solution containing 5.7 g. of ethyl 4-bromo-3-methyl-2-butenate was added dropwise to the so produced solution. After 30 minutes, 100 ml. of 10% aqueous ammonium chloride solution was added, and then the mixture was allowed to stand to reach room temperature. The mixture was subsequently extracted with two 200 ml.

portions of n-hexane. The n-hexane phase was washed with three 100 ml. portions of water, dried, over magnesium sulfate, and evaporated to remove the solvent. There was obtained 14 g. of ethyl 3,7,11,15,19-pentamethyl-5-p-tolylsulfonyl-2,6,10,14,18-eicosapentaenoate.

To 4.1 g. of potassium hydroxide in 50 ml. of isopropyl alcohol was added 12 g. of the above-obtained ethyl 3,7,11,15,19-pentamethyl-5-p-tolylsulfonyl-2,6,10,14,18-eicosapentaenoate, and the mixture was stirred at 50° C. for 3 hours. The reaction liquid was poured into ice-water, made acidic by addition of hydrochloric acid, and extracted with 100 ml. of diethyl ether. The extract was washed with water, dried over magnesium sulfate and evaporated to remove the solvent. There was obtained 8.5 g. of an oil. The so obtained oil was dissolved in 40 ml. of n-hexane and chilled to $-20°$ C. to crystallize. There was obtained 2.3 g. of the desired product as white crystals.

M.p.: 45.5°–46.5° C.

| Analysis for $C_{25}H_{38}O_2$ | | |
|---|---|---|
| | C | H |
| Calculated (%) | 81.03 | 10.34 |
| Found (%) | 80.89 | 10.52 |

NMR spectrum (δ, CDCl$_3$): 1.60 (9H, s), 1.68 (3H, s), 1.86 (3H, s), 1.9–2.3 (12H), 2.33 (3H, s), 5.09 (3H, b), 5.76 (1H, bs), 5.96 (1H, d, J=10 Hz), 6.18 (1H, d, J=15 Hz), 6.89 (1H, dd, J=15 Hz, 10 Hz), 10.2 (1H, b).

Mass spectrum (m/e): 370 (M+).

EXAMPLE 5

Ethyl 3,7,11,15-tetramethyl-2,4,6-hexadecatrienoate

The procedures described in Example 1 were repeated using 6,10,14-trimethyl-3,5-pentadecadien-2-one to obtain the desired product as an oil.

| Analysis for $C_{22}H_{38}O_2$ | | |
|---|---|---|
| | C | H |
| Calculated (%) | 78.98 | 11.45 |
| Found (%) | 79.16 | 11.56 |

NMR spectrum (δ, CDCl$_3$): 0.87 (9H, d, J=7 Hz), 1.27 (3H, t, J=7 Hz), 0.9–1.6 (12H), 1.84 (3H, s), 2.08 (2H, t, J=7 Hz), 2.34 (3H, s), 4.16 (2H, q, J=7 Hz), 5.74 (1H, bs), 5.95 (1H, d, J=11 Hz), 6.16 (1H, d, J=15 Hz), 6.85 (1H, dd, J=15 Hz, 11 Hz).

Mass spectrum (m/e): 334 (M+).

EXAMPLE 6

3,7,11,15-Tetramethyl-2,4,6-hexadecatrienoic acid

The procedures described in Example 2 were repeated using the ethyl 3,7,11,15-tetramethyl-2,4,6-hexadecatrienoate obrained in Example 5 to carry out the hydrolysis. There was obtained the desired product as white crystals.

M.p.: 84.5°–85.5° C.

| Analysis for $C_{20}H_{34}O_2$ | | |
|---|---|---|
| | C | H |
| Calculated (%) | 78.38 | 11.18 |
| Found (%) | 78.35 | 11.21 |

NMR spectrum (δ, CDCl$_3$): 0.87 (9H, d, J=7 Hz), 0.9–1.6 (12H), 1.84 (3H, s), 2.09 (2H, t, J=7 Hz), 2.35 (3H, s), 5.76 (1H, bs), 5.96 (1H, d, J=11 Hz), 6.19 (1H, d, J=15 Hz), 6.90 (1H, dd, J=15 Hz, 11 Hz), 11.5 (1H, b).

Mass spectrum (m/e): 306 (M+).

EXAMPLE 7

3,7,11,15-Tetramethyl-2,4,6,10,14-hexadecapentaenoamide

To a suspension of 5.0 g. of 55% sodium hydride (in oil) in 60 ml. of n-hexane was added 28.6 g. of triethyl phosphonoacetate. The mixture was then heated under reflux, and 20 g. of 6,10,14-trimethyl-3,5,9,13-pentadecatetraen-2-one was added dropwise to the mixture under stirring. After 30 minutes, the reaction liquid was poured into 200 ml. of ice-water, and then 500 ml. of n-hexane was added for extraction. The n-hexane phase was separated, washed with two 100 ml. portions of a mixture of methanol and water (2:1), and concentrated. The so obtained concentrate was purified by silica gel column chromatography to give 18 g. of the desired product as an oil.

To 3.9 g. of potassium hydroxide in 30 ml. of isopropyl alcohol was added 10 g. of the ethyl 3,7,11,15-tetramethyl-2,4,6,10,14-hexadecapentaenoate obtained in the above, and the mixture was stirred at 50° C. for 1 hour. The reaction liquid was poured into ice-water, made acidic by addition of hydrochloric acid, and extracted with 100 ml. of diethyl ether. The ether phase was washed with water, dried over magnesium sulfate and concentrated to give 9.0 g. of an oil. The so obtained oil was dissolved in 50 ml. of n-hexane and chilled to $-20°$ C. to crystallize. There was obtained 4.0 g. of 3,7,11,15-tetramethyl-2,4,6,10,14-hexadecapentaenoic acid as pale yellow needles.

In 20 ml. of diethyl ether was dissolved 3.0 g. of the above-obtained 3,7,11,15-tetramethyl-2,4,6,10,14-hexadecapentaenoic acid. To this solution was added 1 g. of triethylamine, and further added 1.1 g. of ethyl chlorocarbonate under stirring at room temperature. After 10 minutes, gaseous ammonia was introduced into the solution. The reaction liquid was washed with three 10 ml. portions of water, dried over magnesium sulfate, and evaporated to remove the solvent. The residue was purified by alumina column chromatography and crystallized from a mixture of acetone and n-hexane (1:2). There was obtained 1.7 g. of the desired product as pale yellow crystals.

M.p.: 63°–65° C.

| Analysis for $C_{20}H_{31}NO$ | | | |
|---|---|---|---|
| | C | H | N |
| Calculated (%) | 79.67 | 10.37 | 4.65 |
| Found (%) | 79.48 | 10.59 | 4.73 |

NMR spectrum (δ, CDCl$_3$): 1.60 (6H, s), 1.68 (3H, s), 1.84 (3H, d, J=1 Hz), 1.9–2.3 (8H), 2.33 (3H, d, J=1 Hz), 5.08 (2H, m), 5.70 (1H, bs), 5.4–6.1 (2H, b), 5.95 (1H, d, J=11 Hz), 6.15 (1H, d, J=15 Hz), 6.82 (1H, dd, J=15 Hz, 11 Hz).

Mass spectrum (m/e): 301 (M+).

EXAMPLE 8

N-(p-Hydroxyphenyl)-3,7,11,15-tetramethyl-2,4,6,10,14-hexadecapentaenoamide

In 30 ml. of tetrahydrofuran was dissolved 3 g. of 3,7,11,15-tetramethyl-2,4,6,10,14-hexadecapentaenoic acid. To this solution was added 1 g. of triethylamine, and further added 1.1 g. of ethyl chlorocarbonate under stirring at room temperature. After 10 minutes, the reaction liquid was poured into 100 ml. of water, and extracted with 100 ml. of n-hexane. The extract was washed with 50 ml. of water and evaporated to remove the solvent. The residue was dissolved in 30 ml. of tetrahydrofuran. To this soluton was added 1.1. g. of p-aminophenol, and the mixture was stirred at room temperature for 30 minutes. To the reaction liquid was added 200 ml. of diethyl ether, and the mixture was washed successively with two 50 ml. portions of dilute hydrochloric acid and two 50 ml. portions of water. The ether phase was dried over magnesium sulfate and evaporated to remove the solvent. The residue was crystallized from ethanol to obtain 3.2 g. of the desired product as pale yellow crystals.

M.p.: 163°–164° C.

| Analysis for $C_{26}H_{35}NO_2$ | | | |
|---|---|---|---|
| | C | H | N |
| Calculated (%) | 79.34 | 8.96 | 3.56 |
| Found (%) | 79.61 | 8.78 | 3.62 |

NMR spectrum (δ, CDCl$_3$): 1.61 (6H, s), 1.68 (3H, s), 1.85 (3H, s), 1.9–2.3 (8H), 2.38 (3H, s), 5.09 (2H, m), 5.76 (1H, bs), 5.96 (1H, d, J=11 Hz), 6.15 (1H, d, J=15 Hz), 6.42 (1H, b), 6.74 (2H, d, J=8 Hz), 6.82 (1H, d, J=15 Hz, 11 Hz), 7.22 (1H, bs), 7.32 (2H, d, J=8 Hz)

Mass spectrum (m/e): 393 (M+).

EXAMPLE 9

N-Ethyl-3,7,11,15-tetramethyl-2,4,6,10,14-hexadecapentaenoamide 3,7,11,15-Tetramethyl-2,4,6,10,14-hexadecapentaenoic acid and ethylamine were reacted in the same manner as in Example 8 to obtain the desired product as an oil.

| Analysis for $C_{22}H_{35}NO$ | | | |
|---|---|---|---|
| | C | H | N |
| Calculated (%) | 80.19 | 10.71 | 4.25 |
| Found (%) | 80.44 | 10.79 | 4.38 |

NMR spectrum (δ, CDCl$_3$): 1.15 (3H, t, J=7 Hz), 1.60 (6H, s), 1.67 (3H, s), 1.83 (3H, s), 1.9–2.3 (8H), 2.33 (3H, d, J=1 Hz), 3.27 (2H, qd, J=7 Hz, 6 Hz), 5.10 (2H, m), 5.65 (1H, bs), 5.82 (1H, t, J=6 Hz), 5.94 (1H, d, J=11 Hz), 6.10 (1H, d, J=15 Hz), 6.77 (1H, dd, J=15 Hz, 11 Hz).

Mass spectrum (m/e): 329 (M+).

EXAMPLE 10

N,N-Dimethyl-3,7,11,15-tetramethyl-2,4,6,10,14-hexadecapentaenoate 3,7,11,15-Tetramethyl-2,4,6,10,14-hexadecapentaenoic acid and dimethylamine were reacted in the same manner as in Example 8 to obtain the desired product as pale yellow crystals.

M.p.: 39°–39.5° C.

| Analysis for $C_{22}H_{35}NO$ | | | |
|---|---|---|---|
| | C | H | N |
| Calculated (%) | 80.19 | 10.71 | 4.25 |
| Found (%) | 80.26 | 10.83 | 4.32 |

NMR spectrum (δ, CDCl$_3$): 1.60 (6H, s), 1.68 (31 H, s), 1.76 (3H, s), 2.09 (3H, d, J=1 Hz), 1.9–2.3 (8H), 3.00 (3H, s), 3.01 (3H, s), 5.10 (2H, m), 5.93 (1H, bs), 5.94 (1H, d, J=10 Hz), 6.18 (1H, d, J=15 Hz), 6.68 (1H, dd, J=15 Hz, 10 Hz)

Mass spectrum (m/e): 329 (M+).

We claim:

1. A compound having the formula:

$$H\left(\phantom{x}\right)_n\left(\phantom{x}\right)_m A\diagup\!\!\!\diagdown COR$$

in which each of n and m is 0, 1 or 2, n+m is 1 or 2, A is (structures), or (structure), and R is a hydroxyl group, a lower alkoxy group of $$-N{<}^{R_1}_{R_2}$$

wherein each of $R_1$ and $R_2$ represents a hydrogen atom, a lower alkyl group, or an aryl group; provided that R is $$-N{<}^{R_1}_{R_2},$$

if A is (structure), n is 1 and m is 0.

2. A compound as claimed in claim 1 which is 3,7,11,15,19-pentamethyl-2,4,6,10,14,18-eicosahexaenoic acid.

3. A compound as claimed in claim 1 which is 3,7,11,15-tetramethyl-2,4,6,8,10,14-hexadecahexaenoic acid.

4. A compound as claimed in claim 1 which is 3,7,11,15-tetramethyl-2,4,6,14-hexadecatetraenoic acid.

5. A compound as claimed in claim 1 which is N-ethyl-3,7,11,15-tetramethyl-2,4,6,10,14-hexadecapentaenoamide.

6. A compound as claimed in claim 1 which is N-p-hydroxyphenyl-3,7,11,15-tetramethyl-2,4,6,10,14-hexadecapentaenoamide.

* * * * *